(12) United States Patent
Schafer et al.

(10) Patent No.: US 11,719,795 B2
(45) Date of Patent: Aug. 8, 2023

(54) SECTOR VARIABLE TIME GAIN COMPENSATION

(71) Applicant: Accutome Inc., Malvern, PA (US)

(72) Inventors: Mark E. Schafer, Lower Gywnedd, PA (US); Cheng-Ning Chang, North Wales, PA (US); Ross Lefkowitz, Philadelphia, PA (US)

(73) Assignee: Accutome, Inc., Malvern, PA (US)

( * ) Notice: Subject to any disclaimer, the term of this patent is extended or adjusted under 35 U.S.C. 154(b) by 261 days.

(21) Appl. No.: 16/988,004

(22) Filed: Aug. 7, 2020

(65) Prior Publication Data
US 2021/0038187 A1  Feb. 11, 2021

Related U.S. Application Data

(60) Provisional application No. 62/884,461, filed on Aug. 8, 2019.

(51) Int. Cl.
*G01S 7/52* (2006.01)
*A61B 8/08* (2006.01)
(Continued)

(52) U.S. Cl.
CPC ............ *G01S 7/52033* (2013.01); *A61B 8/10* (2013.01); *A61B 8/5207* (2013.01); *A61B 8/4461* (2013.01); *A61B 8/4488* (2013.01)

(58) Field of Classification Search
CPC .. A61B 8/00; A61B 8/10; A61B 8/461; A61B 8/465; A61B 8/467–469;
(Continued)

(56) References Cited

U.S. PATENT DOCUMENTS

| 4,662,380 A | 5/1987 | Riley |
| 4,852,576 A | 8/1989 | Inbar et al. |

(Continued)

FOREIGN PATENT DOCUMENTS

| CN | 110811693 A | 2/2020 |
| EP | 0539697 A1 | 5/1993 |

OTHER PUBLICATIONS

Von Ramm, Olaf T., and Stephen W. Smith. "Beam steering with linear arrays." IEEE transactions on biomedical engineering 8 (1983): 438-452.*

(Continued)

*Primary Examiner* — Carolyn A Pehlke
(74) *Attorney, Agent, or Firm* — Dinsmore & Shohl LLP

(57) ABSTRACT

Ultrasound systems having a computing device, a steering mechanism, and an ultrasound transducer are disclosed. The ultrasound transducer is configured to generate angularly discrete signals over a scan region of the ultrasound system in response to inputs from the steering mechanism. The computing device is communicatively coupled to the ultrasound transducer. The computing device includes a processor configured to receive angularly discrete ultrasound signals from the ultrasound transducer over the scan region, determine a scan line count corresponding to each of the received angularly discrete ultrasound signals, associate a TGC curve with each of the scan line counts, apply a TGC curve to each of the angularly discrete ultrasound signals as associated with the scan line count of each angularly discrete ultrasound signal, where each of the applied TGC curves defines a gain that maintains, increases, or decreases the angularly discrete ultrasound signal to which it is applied, over time.

28 Claims, 6 Drawing Sheets

(51) Int. Cl.
    *A61B 8/00*         (2006.01)
    *A61B 8/10*         (2006.01)

(58) Field of Classification Search
    CPC ..... A61B 8/52; A61B 8/5207; G01S 7/52033;
               G01S 7/489; G01S 7/4918; G01S 7/5345
    See application file for complete search history.

(56) References Cited

U.S. PATENT DOCUMENTS

| | | | |
|---|---|---|---|
| 5,257,624 A | 11/1993 | Fraser et al. | |
| 5,501,221 A | 3/1996 | Foster et al. | |
| 6,102,859 A | 8/2000 | Mo | |
| 6,368,279 B1* | 4/2002 | Liu | G01S 7/52046 |
| | | | 600/443 |
| 2016/0139789 A1* | 5/2016 | Jin | G06T 3/60 |
| | | | 715/771 |
| 2016/0345933 A1* | 12/2016 | Bartlett | A61B 8/5269 |
| 2017/0055953 A1* | 3/2017 | Ohuchi | A61B 8/469 |
| 2018/0177495 A1 | 6/2018 | Kelly et al. | |

OTHER PUBLICATIONS

Ultrasound 101 (www.123sonography.com/blog/ultrasound-101-part-5-gain-and-time-gain-compensation; retrieved Dec. 2, 2022).*
Yu et al. "A programmable time-gain-compensation (TGC) amplifier for medical ultrasonic echo signal processing," URL: https://ieeexplore.ieee.org/document/4734913, Oct. 2008.
International Search Report and Written Opinion of the Internation Searching Authority, dated Jan. 14, 2021.

* cited by examiner

SECTOR VARIABLE TIME GAIN COMPENSATION

CROSS-REFERENCE TO RELATED APPLICATION

This application claims the benefit of U.S. Provisional Application No. 62/884,461, filed Aug. 8, 2019, the entirety of which is hereby incorporated by reference.

TECHNICAL FIELD

The present specification generally relates to ultrasonics, specifically ultrasound medical imaging. More specifically, the subject matter of the present disclosure relates to ultrasound medical imaging of the eye and nearby structures.

BACKGROUND

Ultrasound medical scanning can be used to determine internal eye structures when the normal optical path is blocked, for example, by a cataract. Specifically, ultrasonic scanning can be used for surgical treatment planning in the case of undisclosed conditions which would impact cataract surgery. Ultrasonic scanning can also be used for other applications, such as imaging of ocular tumors, detection of foreign bodies in the eye, and quantification of detached retinas.

In order to serve the largest number of patients, the equipment cost should be kept reasonably low. At the same time, resolving the small structures within the eye often requires that the ultrasound system operate at a relatively high frequency, such as 12-20 MHz. Further, the overall system design must be as simple as possible to meet cost constraints.

Accordingly, there is a need for electronically and/or mechanically steered scanning system that implement scanning sector probes that have the capacity to provide workable solutions to these challenges.

SUMMARY

In one embodiment, an ultrasound system comprises a computing device, a transducer steering mechanism and an ultrasound transducer. The ultrasound transducer is configured to generate angularly discrete signals over a scan region of the ultrasound system under the control of the transducer steering mechanism, for processing by the computing device. The computing device is communicatively coupled to the ultrasound transducer. The computing device includes a processor configured to receive a plurality of angularly discrete ultrasound signals from the ultrasound transducer over the scan region, determine a scan line count corresponding to each of the received plurality of angularly discrete ultrasound signals, associate a Time Gain Compensation (TGC) curve with each of the scan line counts, apply a TGC curve to each of the plurality of angularly discrete ultrasound signals as associated with the scan line count of each angularly discrete ultrasound signal, wherein each of the applied TGC curves defines a gain that maintains, increases, or decreases the angularly discrete ultrasound signal to which it is applied, over the timeframe of a single scan line.

In some embodiments, an ultrasound system comprises a computing device, a transducer steering mechanism, and an ultrasound transducer. The ultrasound transducer is configured to generate angularly discrete signals over a scan region of the ultrasound system under the control of the transducer steering mechanism, for processing by the computing device. The computing device is communicatively coupled to the ultrasound transducer. The computing device includes a processor configured to define a plurality of zones having one or more scan lines within the scan region of the ultrasound transducer, receive a plurality of angularly discrete ultrasound signals from the ultrasound transducer over the scan region, determine a zone corresponding to each of the received plurality of angularly discrete ultrasound signals, associate a Time Gain Compensation (TGC) curve with each of the zones, and apply a TGC curve to each of the plurality of angularly discrete ultrasound signals as associated with the zone of each angularly discrete ultrasound signal, wherein each of the applied TGC curves define a gain that maintains, increases, or decreases the angularly discrete ultrasound signal to which it is applied, over the timeframe of a single scan line.

In some embodiments, an ultrasound system comprising a computing device and an ultrasound transducer. The ultrasound transducer is configured to generate angularly discrete signals over a scan region of the ultrasound system, for processing by the computing device. The computing device is communicatively coupled to the ultrasound transducer. The computing device includes a display, an input device, and a processor, wherein the processor is configured to present, on the display, an ultrasound image, receive, from the input device, designation of one or more regions within the ultrasound image, receive, from the input device, one or more Time Gain Compensation (TGC) curves to associate with the one or more designated regions, receive a plurality of angularly discrete ultrasound signals from the ultrasound transducer over the scan region, determine a zone corresponding to each of the received plurality of angularly discrete ultrasound signals, associate a TGC curve with each of the zones, and apply a TGC curve to each of the plurality of angularly discrete ultrasound signals as associated with the zone of each angularly discrete ultrasound signal, wherein each of the applied TGC curves defines a plurality of gains that maintain, increase, or decrease the angularly discrete ultrasound signal to which it the TGC curve is applied, over the timeframe of a single scan line.

Some embodiments include a method of implementing a TGC pattern that varies with the angular position of an electronic or mechanically steered scanning ultrasound system, using an analog or digital implementation of the TGC.

Some embodiments include a method of implementing a TGC pattern that is symmetric about the central scan line, using an analog or digital implementation of the TGC.

Further embodiments include a method of implementing a TGC pattern that is low-cost, using an analog or digital implementation of the TGC.

BRIEF DESCRIPTION OF THE DRAWINGS

The embodiments set forth in the drawings are illustrative and exemplary in nature and are not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
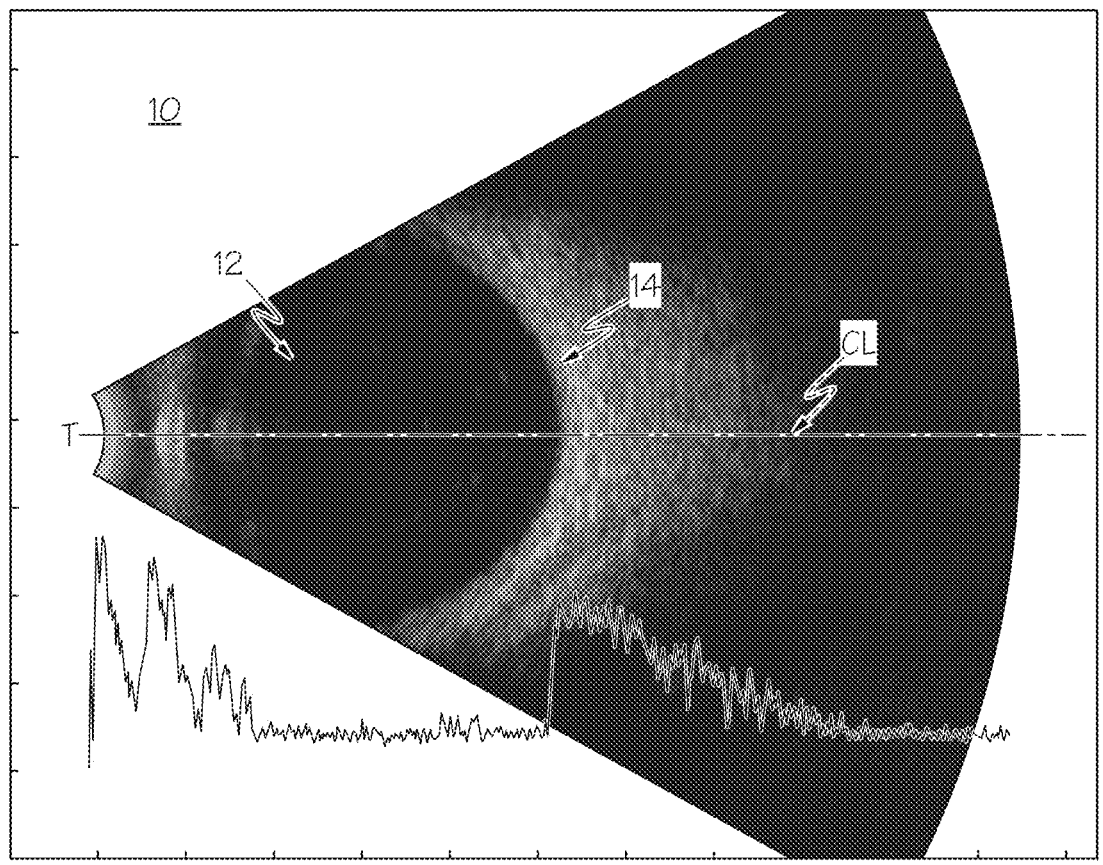
FIG. 1 depicts an illustrative example of an ophthalmic ultrasound image.

Embodiments of the present disclosure include ultrasound imaging processes where the received signals are amplified in order to display them to the operator. Further, since the ultrasound wave is attenuated as it passes through tissue, amplification is increased to compensate for distance traveled. Otherwise, objects or tissue structures further away from the ultrasound source (the transmitter/receiver, or transducer) would be less bright than similar objects or structures closer to the transducer. Thus the amplification is generally increased as a function of display depth. Since the ultrasound wave is assumed to travel at a fixed speed through tissue, time and distance are directly related by the speed of sound within a material. The change in amplification is therefore called Time Gain Compensation (TGC).

There are two possible implementations of TGC, one digital and one analog. For analog TGC, a variable gain amplifier is used in the receiver path between the ultrasound transducer and a logarithmic amplifier. After logarithmic amplification, the signal is digitized and passed to the computing device for display. The gain of the variable gain amplifier is adjusted by applying a time-varying voltage that corresponds to the TGC curve information. For digital TGC, the ultrasound signal is logarithmically amplified and digitized, and the gain of the resultant signal is increased or decreased simply by adding or subtracting digital values.

TGC can be applied uniformly to every ultrasound beam that is used to form an overall image. This simplifies the design of the system as well as provides a less complicated user interface.

In ophthalmic ultrasound imaging, the ultrasound probe can be placed on the front of the eye, on the cornea, and the ultrasound image sector region encompasses the orbit and the rear of the eye. The area to be imaged, which appears generally as a circular structure, is uniform from patient to patient. It is also symmetric about the central axis (i.e., from the center of the probe to the center of the back of the eye). In addition, the image is generally consistent in that the central region of the image has the vitreous, which reflects very little ultrasound compared to the sclera or the rear of the eye.

Accordingly, embodiments of the present disclosure enable selectively higher signal gain in this central region in order to better image the small structure within it, such as "floaters" within the vitreous. Further, the central region comprises vitreous fluid of the eye, which does not generally reflect ultrasound (i.e., vitreous fluid is anechoic). However, applying this higher gain to the edges of the image, which may constitute the sclera, can lead to unacceptable bright regions which distract from the observation of details in the center.

Therefore, a need for TGC that varies not only in depth, but also as a function of angle is implemented in embodiments of the present disclosure. In this way, the central region could have a TGC more appropriate to imaging small scatterers in the midst of anechoic fluid, while the edges of the image would have a different TGC that is appropriate to solid tissue reflections. For example, the gain values of the TGC curve are configured to vary as a function of radial distance from the transducer. Furthermore, one or more TGC curves may be applied to ultrasound signals based on the scan line count. Embodiments and examples will be described in more detail herein.

Furthermore, embodiments include methods for providing TGC that varies across the scanned region. For the particular case of scanning the human eye, the angular pattern of said TGC can be symmetric about the central scan line, since the eye itself is generally symmetric about the central axis. The methods may be suitable for implementation in mechanically scanned ultrasound imaging systems, as these predominate the ophthalmic market, for reasons noted earlier. The implementation of various TGCs can be done at a low cost, in order to serve markets in developing nations.

The following will now describe the systems and methods in more detail with reference to the drawings where like numbers refer to like structures.

Referring now to the drawings, FIG. 1 is an illustrative example of an ophthalmic ultrasound image 10. The ultrasound sector scanner having a transducer is positioned (e.g., at position "T") to the left and the eye is clearly seen to the right. The darkened circular area 12 represents the internal vitreous portion of the eye where higher gain would be appropriate. In this particular image, the sides of the scan do not include the sclera. Note that the back of the eye 14 is circularly shaped, but the circle is not centered on the rotational pivot point of the ultrasound scanner. Therefore, portions of the back of the eye at the edges of the scan are closer to the transducer than portions of the back of the eye at the center of the scan. In order to have a uniform brightness over the entire back of the eye, while maintaining high gain in the vitreous region, a gain pattern that has different TGC curves as a function of scan angle is needed. It is also clear from this image that the image of the eye appears very symmetric about the center line "CL" of the scan, shown as a black line.

Figure 2:
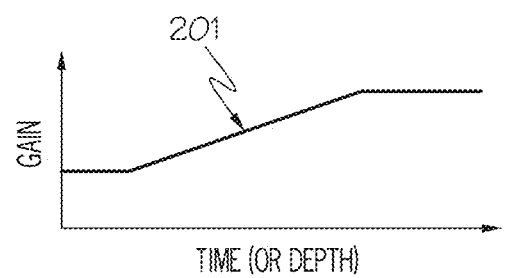
FIG. 2 depicts an illustrative TGC curve where the gain or amplification of the received signal increases as a function of time, according to one or more embodiments shown and described herein.

FIG. 2 shows a Time Gain Compensation curve where the gain or amplification of the received signal increases as a function of time. The curve 201 indicates the regions that will have lower gain and higher gain, and the rate of increase between these regions (e.g., illustrated by the slopes of the line). Since ultrasound waves travel with a fixed speed of sound within soft tissue (with some minor variability), the time axis also represents distance or depth into the tissue. That is, the gain profile which includes a plurality of gain values as a function of time designated for a particular angle of the scan region with reference to the transducer's position may be applied to the received ultrasound echo signal based on the time from transmission to receipt by the transducer.

Figure 3:
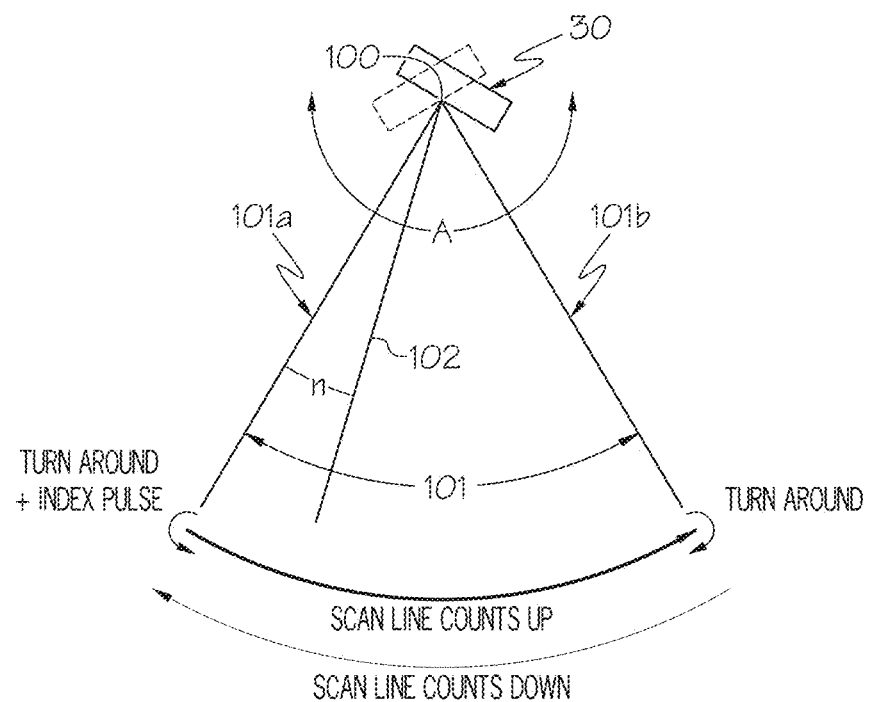
FIG. 3 depicts an illustrative motion pattern of an ultrasound sector scan probe, according to one or more embodiments shown and described herein.

FIG. 3 shows the motional pattern of an ultrasound sector scan probe. The ultrasound transducer 30 is located at position 100, the apex of the imaging sector. The transducer 30 sweeps back and forth (arrow A) over a scan region 101 as it sweeps through multiple scan angles from position 101a to 101b. As shown, it turns around at the edges. There are multiple ultrasound transmit/receive instances as the transducer 30 moves from 101a to 101b. Each transmit/receive instance generates a scan line 102. The angular position (n) of each scan line 102 is required so that the ultrasound imaging system can reconstruct a two dimensional cross sectional image (as shown in FIG. 1), with the proper spatial alignment. Thus, each scan line 102 is assigned a numeric value (e.g., a scan line count (n)) that can be matched to a specific angular orientation. The scan line count may be counted upwards from the position 101a to a maximum count at position 101b. When the transducer 30 sweeps from position 101b to position 101a, the scan line count counts down from the maximum back down to zero. In this manner, scan lines that have the same angular orientation are given the same scan line count. For instance, a system which has 128 scan lines per image would start at scan line 0 at position 101a, and the scanline count would increment until the transducer 30 was oriented to position 101b, with scan line count 127. After the transducer 30 angular motion stopped and reversed (in the angular region beyond position 101b), the scanline count would resume at count 127 (when the transducer was again oriented to position 101b) and would decrement to 0 upon reaching position 101a.

In some embodiments, each scan line or a group of scan lines may have a predetermined TGC curve (i.e., gain profile) assigned to it. The TGC curve includes one or more gain values that are applied to the ultrasound signal received by the transducer 30. As described in more detail herein, a user may preconfigure first region of a scan to have a first TGC curve and a second region to have a second TGC curve. In some instances, a user may complete an initial scan and subsequently update one or more of the TGC curves or one or more gain values within the one or more TGC curves to improve the visibility of structures through an increase or decrease in the gain applied to ultrasound signals captured during a subsequent scan.

Figure 4:
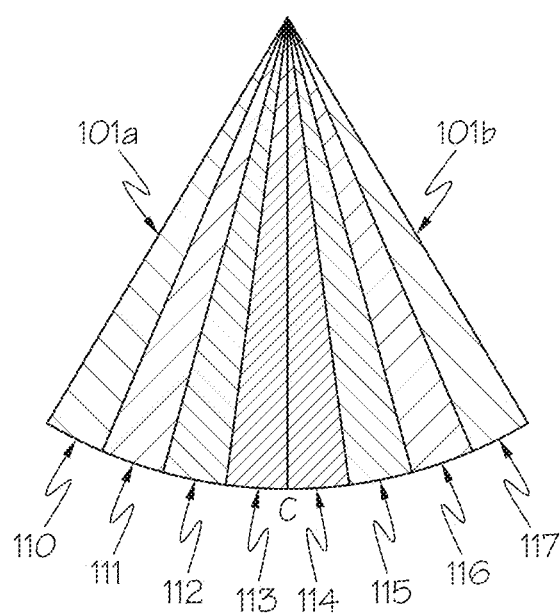
FIG. 4 depicts an illustrative representation of different zones within the scan region having independent TGC curves, according to one or more embodiments shown and described herein.
Figure 5A:
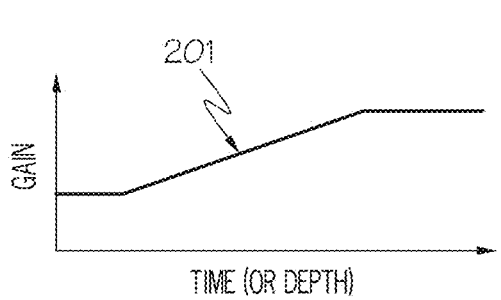
FIG. 5A depicts a first illustrative TGC curve, according to one or more embodiments shown and described herein.
Figure 5B:
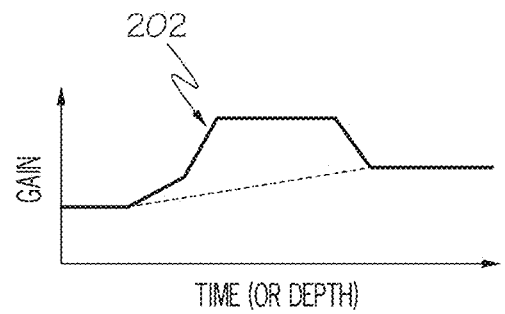
FIG. 5B depicts a second illustrative TGC curve, according to one or more embodiments shown and described herein.
Figure 5C:
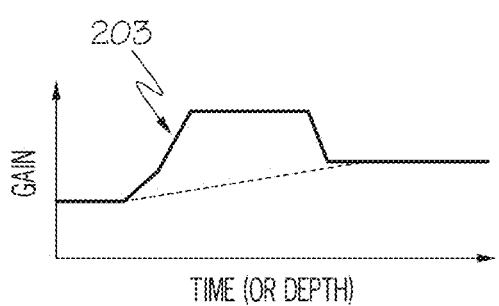
FIG. 5C depicts a third illustrative TGC curve, according to one or more embodiments shown and described herein.
Figure 5D:
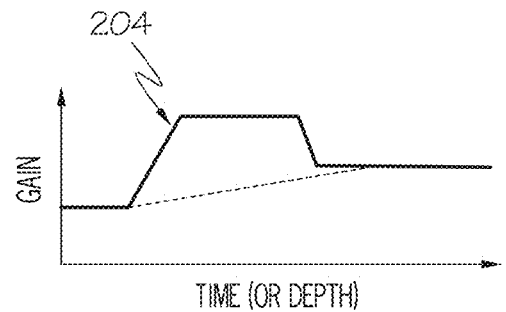
FIG. 5D depicts a fourth illustrative TGC curve, according to one or more embodiments shown and described herein.

FIG. 4 shows an example of different zones (also referred to herein as predefined angular orientation ranges) within the scan region 101, with independent TGC curves. In this example, there are 8 zones, positioned symmetrically about the central axis (C) of the scan. Elements 110 through 117 designated the 8 zones. Because of the symmetry, there are only 4 distinct TGC curves, as zones 110 and 117 are the same, 111 and 116 are the same, 112 and 115 are the same, and 113 and 114 are the same.

FIGS. 5A-5D shows examples of different possible TGC curves that may be used in the different zones. For example, TGC curve 201 may be used in zones 110 and 117, TGC curve 202 may be used in zones 111 and 116, TGC curve 203 may be used in zones 112 and 115, and TGC curve 204 may be used in zones 113 and 114. Moreover, a user may define a TGC curve with a computing device and subsequently assign a predefined TGC curve to a zone and/or one or more scan lines.

As the ultrasound transducer 30 at position 100 is mechanically or electronically sector scanned over some scan angle, as shown in FIG. 4, ultrasound waves are repetitively emitted and received by the transducer 30 to produce scan lines in order to create an ultrasound image such as the ultrasound image depicted in FIG. 1. Each scan line has a unique number (e.g., a scan line count), for example, from 0 to 127. Those skilled in the art would appreciate that there can be more or fewer total scan lines in an image. From FIG. 1, it can be understood that the proper amplification necessary to image certain tissues is different as a function of angle across the image. The back of the eye, for instance, is much more highly reflective than the center of the eye which contains the vitreous. The back of the eye is also curved, but the center of curvature is not the same as the center of rotation of the ultrasound transducer 30. Therefore, the back of the eye is not equidistant from the transducer as a function of angle, as can be seen in FIG. 1. Therefore, the amplification necessary for the back of the eye must not only be lower than for the vitreous region, but it also should account for the variation in the distance from the transducer 30 to the back of the eye.

As the transducer 30 sweeps through angles of defining the scan region, the TGC curve is changed to accommodate the change in position of the back of the eye. Specifically, zone 110, with TGC curve 201 may be used first. While not seen in FIG. 1, those skilled in the art would understand that zone 110 would often include the sclera of the eye, and thus the TGC curve may not have large gain in the middle depth regions. As the transducer 30 continues to sweep and the transducer angle changes, zone 110 may be amplified using TGC curve 202. This TGC curve has substantially higher gain in the middle depth region, corresponding to the vitreous. The gain is reduced back down at the far depth region where the back of the eye is located.

Continuing the sweep pattern, the zone and corresponding TGC curve change again, providing high gain in the vitreous region but reducing the gain for the back of the eye at slightly shallower depths, as seen in FIGS. 4 and 5, with TGC curves 203 and 204.

As the transducer continues past the midpoint of the sweep, the pattern reverses to maintain symmetry, changing the TGC curves from 204, to 203, to 202, and finally to 201. When the transducer reaches position 101b, turns around and sweeps back, as shown in FIG. 3, the process repeats.

Figure 6:
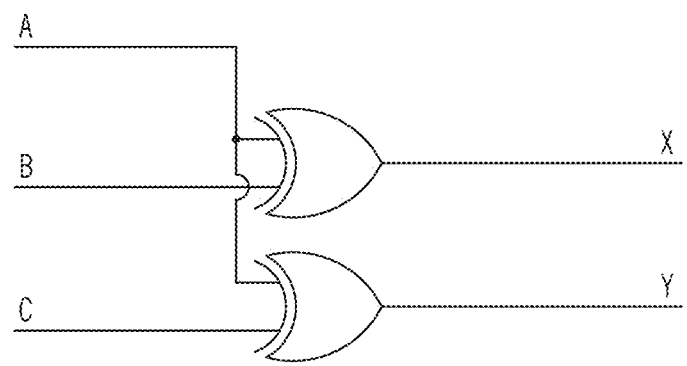
FIG. 6 depicts an example schematic of a logic circuit to select a predetermined TGC curve with a scan line based on the scan line count, according to one or more embodiments shown and described herein.

An ultrasound system 400, as depicted and described in more detail with reference to FIG. 9, may implement software and/or hardware logic to determine and apply a predetermined TGC curve with a scan line or zone based on the scan line count. FIG. 6 shows an example logic circuit to convert a scan line count into a TGC curve address. In this example, the highest three bits "ABC" of the 7-bit scan line counter (e.g., one bit defining one of each of the 128 scan positions) would be used to count the four zones. This logic circuit produces a count that enumerates the zones symmetrically about the center location of the 128 scan line positions. However, one skilled in the art may know to implement alternative logic circuits in view of this teaching to correlate various scan line counts and zones in alternative embodiments.

In order to implement these zones and TGC curves, the scan line counter is used to create the zone addresses using a conversion, for example, of the type shown in the following table.

| Highest bits from Scan Line Counter e.g. 100 => 0b1100100 (ABC = 110) | Zone Counter (XY) |
|---|---|
| 000 | 00 |
| 001 | 01 |
| 010 | 10 |
| 011 | 11 |
| 100 | 11 |
| 101 | 10 |
| 110 | 01 |
| 111 | 00 |

For example, if there are 128 scan lines in the image, a 7 bit representation of the scan line count may be used to represent each scan line in binary for the logic circuit. Moreover, depending on the number of zones that are defined, a predetermined number of bits of the 7 bit representation may be used. For example, in the embodiments depicted herein there are 4 zones so the highest 3 bits would be used. Moreover, for example, if more or fewer scan lines were implemented, requiring 8 or 6 bit representation, the highest 3 bits may still be used. From those three bits, the two bit zone counter can be derived by using the logic implementation shown in FIG. 6. One skilled in the art would appreciate that this circuit can be modified to account for differing numbers of zones.

By way of example, scan line count 100 is represented in 7-bit binary form as 1100100. The three highest bits are 110. These bits may be fed into the logic circuit as follows, the highest bit into input A, the second highest bit into input B, and the third highest bit into input C. That is, 1➔A, 1➔B, and 0➔C. The logic circuit is configured as a set of XOR gates such that XOR(A,B)=X and XOR(A,C)=Y, where XY designates the zone thus the TGC curve assigned to that zone.

By way of a further example, a zone counter is used as the highest address bits of the overall TGC digital memory. In an embodiment, the TGC memory is organized as 4 banks of 256 bytes. The 256 bytes encode the various TGC curves, such as 201, 202, 203, and 204. The memory position within the 256 bytes corresponds to a time position along the TGC curve. The memory contents are read out as input to a Digital to Analog Converter (DAC), which produces an analog voltage that controls the analog gain function. The rate at which the 256 bytes are read out produces the time increment between TGC samples. In an embodiment, that rate can be 0.75 MHz, although one skilled in the art would appreciate that the rate is set such that the total number of bytes corresponds to the deepest portion of the image. The number of bytes can similarly be changed as appropriate. Other factors which influence the choice of the number of bytes and the read rate include the speed of the DAC and the desired resolution of the TGC curve, as well as the total scan depth.

Aspects of the present disclosure relate to the implementation of varying Time Gain Compensation curves in a symmetric manner within a mechanically scanned ultrasound image, in a manner that is easily implemented for low cost systems. The disclosed implementation takes unique advantage of the symmetry of the image of the eye, and exploits it to allow for a few zones to be used to improve the imaging of the vitreous region. Disclosed implementations can also provide for a straightforward implementation that requires little computational power. Particular embodiments may require only 1 kB of memory, organized as 4 by 256 bytes, to produce the zones such as those shown in FIG. 4. Further, the addressing scheme as described can be easily accomplished with logic functions, as shown in FIG. 6.

Figure 7:
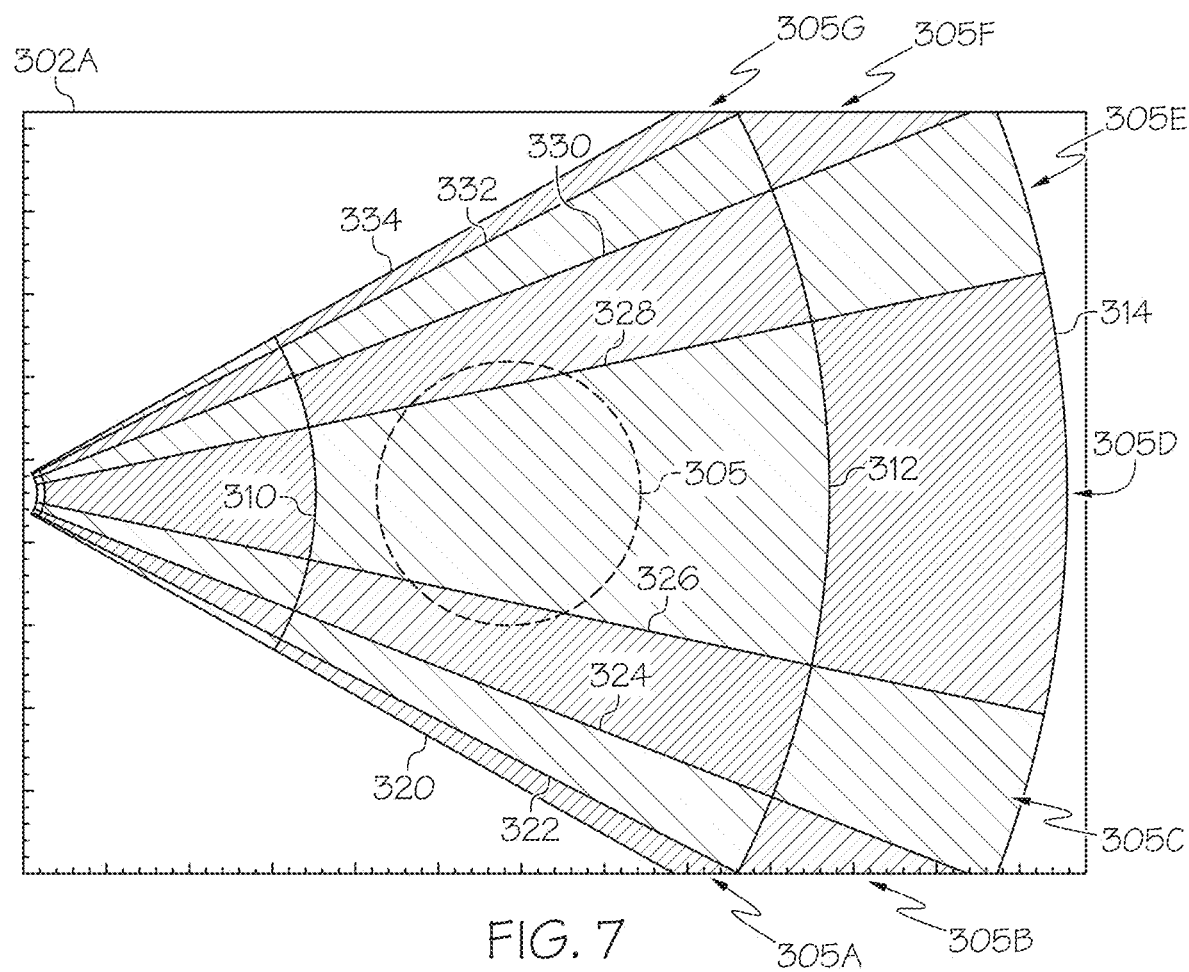
FIG. 7 depicts an illustrative example of a display (e.g., a touchscreen interface) having selectable portions within zones, according to one or more embodiments shown and described herein.

Aspects of the present disclosure provide novel ways of allowing a user to control the TGC of an image. Referring to FIG. 7 an illustrative example of a display 402a (FIG. 9) (e.g., a touchscreen interface) having selectable regions within zones predefined for an ultrasound image is depicted. That is, the computing device may present an interactive image of a scan region of the transducer. In some embodiments, the ultrasound scan region is overlaid on a previously captured ultrasound image captured by the ultrasound device. For instance, a touchscreen interface would allow the user to designate a region of the image, for example, the central circular region comprising the vitreous, to have a higher gain than the outermost regions. The designated region would be mapped onto the zones, and each zone would be adjusted accordingly to produce the desired regional gain effect. Accordingly, a user may configure TGC curves in real time based on observed structures from a previous ultrasound image. Configuring the TGC curves in view of the previous ultrasound image allows a user to select regions that need an increase or decrease in gain to better observe structures of interest.

In some embodiments, the display 302a displays a real-time or near real-time ultrasound image generated from the ultrasound probe and transducer. As the ultrasound image is presented on the display 302a, a user of the ultrasound system may select predefined regions or zones 305A-305G or generate custom regions such as a user defined region 305. Once regions are defined and selected the user may adjust gain values for the TGC curves corresponding to the selected regions. This may be done in real-time or near real-time with live images generated by the ultrasound system or a user may pause or freeze a current ultrasound image to select portions that the user desires to update.

In other embodiments, a user may use a input device (e.g., 402c, FIG. 9) such as a stylus, a finger on a touchscreen interface, a mouse, a keyboard, or other input device to trace out, for example, an user defined region 305 and define a gain value for implementation in the one or more TGC curves defining the user defined region.

The test pattern depicted on the display 402a is an illustrative example of different TGC curves being applied to predefined zones 305A-305G, defined as portions extending radially from the transducer and covering an angular region of the scan region. As described herein, each zone may be assigned a TGC curve that defines one or more gain values to be assigned to the signals obtained from a scan within that zone as a function of time, which corresponds to depth. Arcs 310, 312, and 314 illustrate three different depths of an ultrasound scan and when bounded by the scan lines 320, 322, 324, 326, 328, 330, 332, 334 defining the angular distance from the edge of a scan region, a plurality of regions are defined.

The TGC in each successive region within a zone (e.g., zone 305A) is a pattern of maximum gain (bright regions) or minimum gain (dark regions). The maximum and minimum gains illustrated are merely example and are not indicative of clinical use. Adjacent zones have inverted patterns, so it may be clearly illustrated as to where each pattern starts and ends.

Figure 8A:
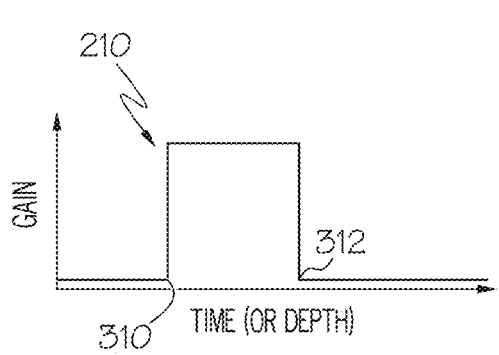
FIG. 8A illustrates a TGC curve used to create a portion of the test pattern depicted in FIG. 7, according to one or more embodiments shown and described herein.
Figure 8B:
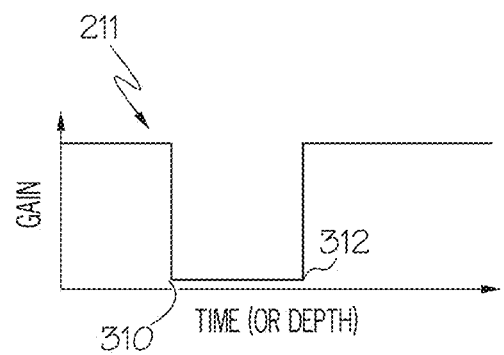
FIG. 8B illustrates another TGC curve used to create another portion of the test pattern depicted in FIG. 7, according to one or more embodiments shown and described herein.

The different regions have been set up to provide either the maximum gain (which produces bright/white image areas) or minimum gain (which produces dark/black image areas). These specific TGC patterns are shown in FIG. 8. These patterns would not be clinically useful, but were set up in order to demonstrate the different zones as clearly as possible.

For example, lower edge of the image in FIG. 7 implements TGC curve 211 (FIG. 8B) for a fixed number of scan lines defined by zone 305A. The next zone 305B implements TGC curve 210 (FIG. 8A) 210, then zone 305C implements TGC curve 211 (FIG. 8B), and then to zone 305D which implements TGC curve 210. The pattern then repeated as a mirror image over zone 305D. The outermost TGC regions in this image are narrower than those illustrated in FIG. 4 because the scan region is limited to less than the full 128 scan lines.

As discussed above, FIGS. 8A and 8B illustrate TGC curves used to create the test pattern depicted in FIG. 7. TGC curve 210 starts with minimal gain, then goes to maximum gain after a first time (depth) is passed denoted by arc 310, then returns to minimum gain after a second time (depth) is passed denoted by arc 312. TGC curve 211 starts with maximum gain, then goes to minimum gain after a first time (depth) is passed denoted by arc 310, then returns to maximum gain a second time (depth) is passed denoted by arc 312. As described herein, a user may define the gain values within a predefined region 305A-305G or a user defined region 305 using a computing device 402 (FIG. 9) and/or a display 402a (e.g., a touchscreen) configured as part of the ultrasound system. Furthermore, the gain values within region may be a fixed value or may be further be a function of time (depth) from the transducer.

Figure 9:
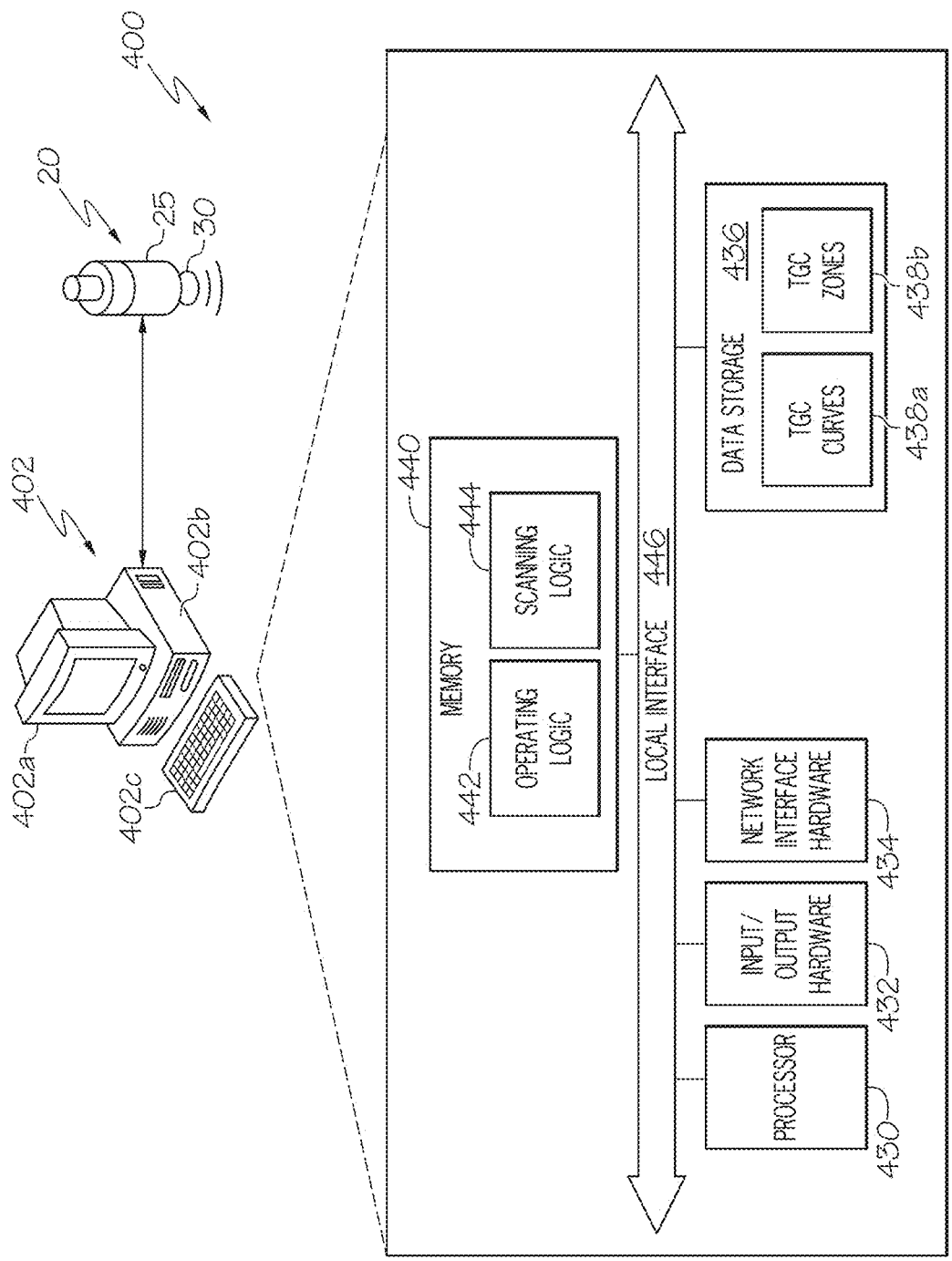
FIG. 9 depicts an illustrative ultrasound system, according to one or more embodiments shown and described herein.

Referring now to FIG. 9, an illustrative ultrasound system 400 is depicted. The ultrasound system includes an ultrasound scanning probe 20 having a steering mechanism 25 that steers an ultrasound transducer 30. The ultrasound scanning probe 20 and the ultrasound transducer 30 may be communicatively coupled to a computing device 402. The ultrasound transducer 30 is any device capable of emitting and receiving ultrasound signals. The steering mechanism may be an electronically or mechanically driven mechanism. For example, an electronically driven mechanism may include an electronic circuit that is configured to cause portions of a linear or curved transducer array to emit and receive ultrasound signals. A mechanically driven mechanism may include a motor or other driving means coupled to a pivot, cam, or the like to cause a transducer to sweep across an angular region such as a scan region while emitting and receiving ultrasound signals. That is, the ultrasound transducer 30 may be configured to mechanically oscillate over a predefined angular region to enable an ultrasound scan of material such as an eye. The ultrasound transducer 30 may include a mechanical angular actuator such that the angularly discrete ultrasound signals are enabled by mechanical scanning. In some embodiments, the ultrasound transducer 30 may be a multi-element array transducer that generates the angularly discrete ultrasound signals through electronic scanning. Whether the ultrasound transducer 30 is mechanically and/or electronically driven to scan an angular region the ultrasound transducer 30 is configured to emit and/or receive an ultrasound signal at a predefined frequency and position, which may be controlled and/or tracked by the computing device 402. In other words, the angular position of the ultrasound transducer 30 is determined and tracked by the computing device 402. Moreover, as described above, the angular position of the ultrasound transducer 30 corresponds to a scan line count so that the computing device may determine which TGC curve has been assigned to the particular scan line count within the scan region. Similarly, in an electronically driven transducer system, the scan line count corresponds to the angular position of the ultrasound beam emitted by the active portion of the multi-element array in response to the electronic control provided through the electronically driven steering mechanism.

The computing device 402 may be used to control the ultrasound transducer and/or receive signals from the transducer to generate ultrasound images. The computing device may be a conventional computer or any other electronic control unit capable of controlling the ultrasound transducer 30 to produce ultrasound images according to the embodiments disclosed herein. As depicted and described herein, the computing device 402 may utilize hardware, software, and/or firmware, according to embodiments shown and described herein. While in some embodiments, the computing device 402 may be configured as a general-purpose computer with the requisite hardware, software, and/or firmware, in some embodiments, the computing device 402 may be configured as a special purpose computer designed specifically for performing the functionality described herein.

The computing device 402 may include a display 402a, a processing unit 402b and an input device 402c. The display 402a may be a touchscreen interface or any other display capable of presenting data and/or images to a user. The input device 402c may be a keyboard, mouse, stylus, touchpad or the any other hardware device capable of translating user action into a computing command. The computing device 402 may include a processor 430, input/output hardware 432, network interface hardware 434, a data storage component 436, which store TGC curves 438a, TGC zones 438b, and other ultrasound data, and a memory component 440. The memory component 440 may be machine-readable memory (which may also be referred to as a non-transitory processor readable memory). The memory component 440 may be configured as volatile and/or nonvolatile memory and, as such, may include random access memory (including SRAM, DRAM, and/or other types of random access memory), flash memory, registers, compact discs (CD), digital versatile discs (DVD), and/or other types of storage components. Additionally, the memory component 440 may be configured to store operating logic 442, scanning logic 444 (each of which may be embodied as a computer program, firmware, or hardware, as an example). A local interface 446 is also included in FIG. 9 and may be implemented as a bus or other interface to facilitate communication among the components of the computing device 402.

The processor 430 may include any processing component(s) configured to receive and execute programming instructions (such as from the data storage component 436 and/or the memory component 440). The instructions may be in the form of a machine-readable instruction set stored in the data storage component 436 and/or the memory component 440. The processor 430 may also be referred to herein as an electronic control unit. The input/output hardware 432 may include a monitor, keyboard, mouse, printer, camera, microphone, speaker, and/or other device for receiving, sending, and/or presenting data. The network interface hardware 434 may include any wired or wireless networking hardware, such as a modem, LAN port, WiFi card, WiMax card, mobile communications hardware, and/or other hardware for communicating with other networks and/or devices.

It should be understood that the data storage component 436 may reside local to and/or remote from the computing device 402 and may be configured to store one or more pieces of data for access by the computing device 402 and/or other components. As illustrated in FIG. 9, the data storage component 436 stores TGC curves 438a and TGC zones 438b. The TGC curves 438a are the gain profiles discussed above that are applied to ultrasound signals received by the transducer 30. The TGC zones 438b are the zones defined by the scan regions and/or the scan line counts. The TGC zones 438b may also include a configuration file that assigns a particular TGC curve to a zone. This may be stored as an assignment table or look-up table having information such as depicted in Table 1.

Still referring to FIG. 9, included in the memory component 440 are the operating logic 442 and scanning logic 444. The operating logic 442 may include an operating system and/or other software for managing components of the computing device 103. The scanning logic 444 may be logic configured to carry out an ultrasound scan and apply a predefined TGC curve to the received ultrasound signals as defined by the user. The scanning logic 444 may also be configured to enable a user to define or customize TGC curves, zones, or other properties and/or functions of the ultrasound system 400.

It should be understood that the components illustrated in FIG. 9 are merely exemplary and are not intended to limit the scope of this disclosure. More specifically, while the components in FIG. 9 are illustrated as residing within the computing device 402, this is merely an example. In some embodiments, one or more of the components may reside external to the computing device 402.

Figure 10:
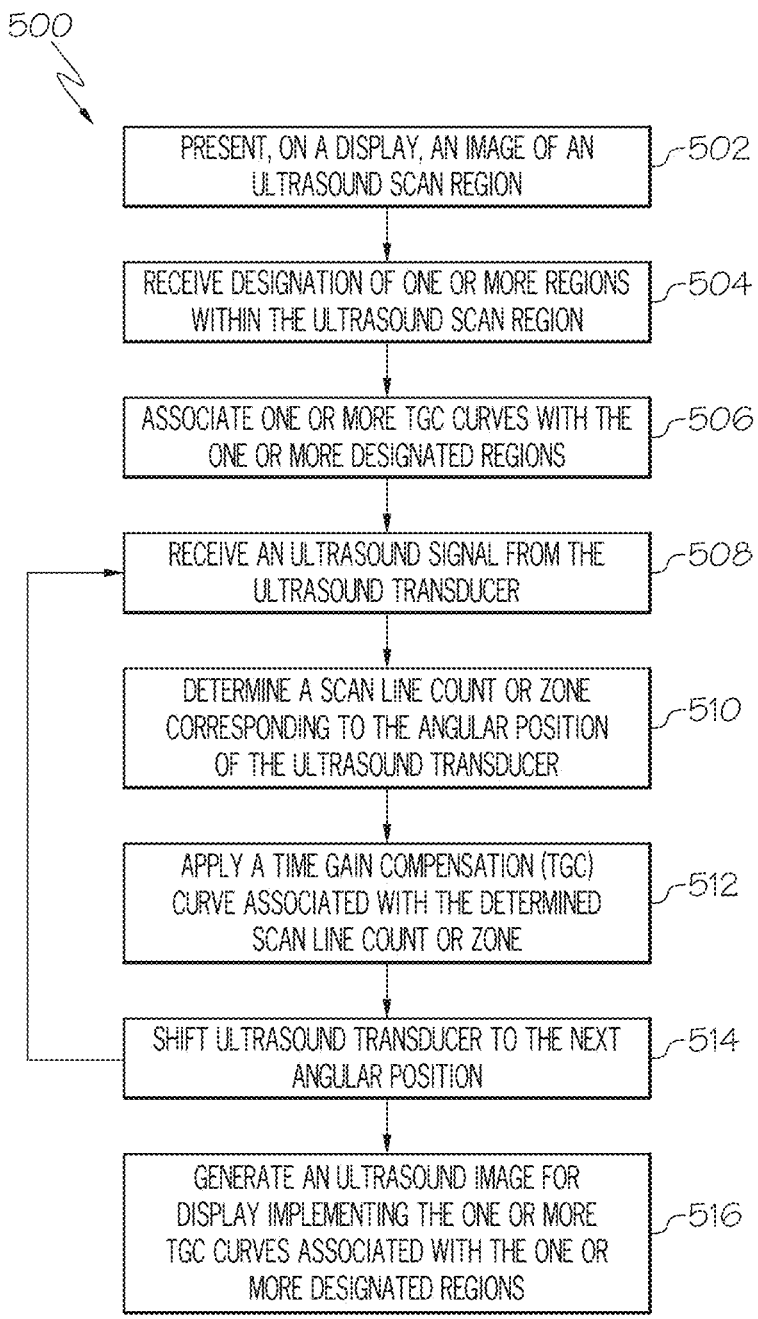
FIG. 10 depicts an illustrative method of implementing an ultrasound scan using TGC curves is, according to one or more embodiments shown and described herein.

Referring now to FIG. 10, an illustrative method of implementing an ultrasound scan using TGC curves is depicted. As described above, the method may be carried out by a computing device 402. The flow diagram 500 depicted in FIG. 10 is a representation of a machine-readable instruction set stored in the non-transitory computer readable memory 440 (FIG. 9) and executed by the processor 430 (FIG. 9) of the computing device 402. The process of the flow diagram 500 in FIG. 10 may be executed at various times and repeated with various types of environments.

In some embodiments, a user may interface with the ultrasound system via a computing device to configure the system to generate an ultrasound image with gains to improve the visibility of structures that the transducer is scanning. Accordingly, a computing device (402, FIG. 9) may be configured to present an image of an ultrasound scan region on a display (402a, FIG. 9). The ultrasound scan region may have predefined regions that define zones and/or scan lines that are selectable. Once selected, a user may designate a TGC curve to apply to the zone and/or scan line and/or provide updates to automatically assigned TGC curves. That is, at block 504 the computing device may receive from a user a designation of one or more regions within the ultrasound scan region and at block 506 associate one or more TGC curves with the selected regions. In some embodiments, the regions may be user defined. That is, the user may use an input device such as a touchscreen interface to draw a region of interest on the ultrasound scan region and assign a desired TGC curve or update the gain values of the one or more TGC curves associated to that region. In some instances, a previously captured ultrasound image may also be displayed so that a user can select regions according to the structures of interest that they wish to obtain further images of.

At block 508, the computing device 402 receives an ultrasound signal from the ultrasound transducer (30, FIG. 9) positioned to transmit and receive a signal at a first angular position. The angular position may be known by the computing device as a function of an encoder or other position tracking signals and system as part of the ultrasound probe. The ultrasound transducer's 30 position corresponds to a scan line count that the computing device determines through segmenting the scan region with a predetermined number of scan lines, for example 128. The scan lines may also be grouped together into zones. At block 510, the computing device 402 may either determine a scan line count or a zone corresponding to the angular position of the transducer when the transducer generated the received ultrasound signal. At block 512, the computing device 402 applies the TGC curve that is associated with the ultrasound signal so that one or more gains maintain, increase, or decrease the ultrasound signal's brightness as a function of depth, thus improving visibility of an inspected structure or material.

At block 514, the transducer 30 may shift its angular position and perform a subsequent receive sequence, thus returning the process to block 508. The scanning process may loop any number of times until a sufficient number of ultrasound signals are obtained to generate an ultrasound image. Accordingly, at block 516, the ultrasound system 400 with the computing device 402 may generate an ultrasound image for display. The ultrasound image implements the one or more TGC curves associated with the one or more designated regions.

The functional blocks and/or flowchart elements described herein may be translated onto machine-readable instructions or as a computer program product, which when executed by a computing device, causes the computing device to carry out the functions of the blocks. As non-limiting examples, the machine-readable instructions may be written using any programming protocol, such as: descriptive text to be parsed (e.g., such as hypertext markup language, extensible markup language, etc.), (ii) assembly language, (iii) object code generated from source code by a compiler, (iv) source code written using syntax from any suitable programming language for execution by an interpreter, (v) source code for compilation and execution by a just-in-time compiler, etc. Alternatively, the machine-readable instructions may be written in a hardware description language (HDL), such as logic implemented via either a field programmable gate array (FPGA) configuration or an application-specific integrated circuit (ASIC), or their equivalents. Accordingly, the functionality described herein may be implemented in any conventional computer programming language, as pre-programmed hardware elements, or as a combination of hardware and software components.

It should now be understood that an ultrasound system includes a computing device, a transducer steering mechanism, and an ultrasound transducer. The computing device is communicatively coupled to the ultrasound transducer. The computing device includes a processor configured to receive an ultrasound signal from the ultrasound transducer at a first angular position, determine a scan line count corresponding to the received ultrasound signal based on the first angular position of the ultrasound transducer, and apply a time gain compensation (TGC) curve associated with the determined scan line count to the ultrasound signal, wherein the TGC curve defines a plurality of gains that maintain, increase, or decrease the ultrasound signal received by the ultrasound transducer, over time at the first angular position of the ultrasound transducer.

It should be further understood that an ultrasound system comprising a computing device, a transducer steering mechanism, and an ultrasound transducer, where the ultrasound transducer is configured to generate angularly discrete signals over a scan region of the ultrasound system, for processing by the computing device; the computing device is communicatively coupled to the ultrasound transducer; and the computing device includes a processor configured to receive a plurality of angularly discrete ultrasound signals from the ultrasound transducer over the scan region at a first angular position, determine scan line counts corresponding to the received plurality of angularly discrete ultrasound signals, and apply time gain compensation (TGC) curves associated with the determined scan line counts to the plurality of angularly discrete ultrasound signal, wherein the TGC curves define a plurality of gains that maintain, increase, or decrease one or more of the plurality of angularly discrete ultrasound signals received by the ultrasound transducer, over the timeframe of a single scan line.

Additionally, in some embodiments, an ultrasound system comprises a computing device, a transducer steering mechanism and an ultrasound transducer. The ultrasound transducer is configured to generate angularly discrete signals over a scan region of the ultrasound system under the control of the transducer steering mechanism, for processing by the computing device. The computing device is communicatively coupled to the ultrasound transducer. The computing device includes a processor configured to receive a plurality of angularly discrete ultrasound signals from the ultrasound transducer over the scan region, determine a scan line count corresponding to each of the received plurality of angularly discrete ultrasound signals, associate a Time Gain Compensation (TGC) curve with each of the scan line counts, apply a TGC curve to each of the plurality of angularly discrete ultrasound signals as associated with the scan line count of each angularly discrete ultrasound signal, wherein each of the applied TGC curves defines a gain that maintains, increases, or decreases the angularly discrete ultrasound signal to which it is applied, over the timeframe of a single scan line.

In some embodiments, an ultrasound system comprises a computing device, a transducer steering mechanism, and an ultrasound transducer. The ultrasound transducer is configured to generate angularly discrete signals over a scan region of the ultrasound system under the control of the transducer steering mechanism, for processing by the computing device. The computing device is communicatively coupled to the ultrasound transducer. The computing device includes a processor configured to define a plurality of zones having one or more scan lines within the scan region of the ultrasound transducer, receive a plurality of angularly discrete ultrasound signals from the ultrasound transducer over the scan region, determine a zone corresponding to each of the received plurality of angularly discrete ultrasound signals, associate a Time Gain Compensation (TGC) curve with each of the zones, and apply a TGC curve to each of the plurality of angularly discrete ultrasound signals as associated with the zone of each angularly discrete ultrasound signal, wherein each of the applied TGC curves define a gain that maintains, increases, or decreases the angularly discrete ultrasound signal to which it is applied, over the timeframe of a single scan line.

In some embodiments, an ultrasound system comprising a computing device and an ultrasound transducer. The ultrasound transducer is configured to generate angularly discrete signals over a scan region of the ultrasound system, for processing by the computing device. The computing device is communicatively coupled to the ultrasound transducer. The computing device includes a display, an input device, and a processor, wherein the processor is configured to present, on the display, an ultrasound image, receive, from the input device, designation of one or more regions within the ultrasound image, receive, from the input device, one or more Time Gain Compensation (TGC) curves to associate with the one or more designated regions, receive a plurality of angularly discrete ultrasound signals from the ultrasound transducer over the scan region, determine a zone corresponding to each of the received plurality of angularly discrete ultrasound signals, associate a TGC curve with each of the zones, and apply a TGC curve to each of the plurality of angularly discrete ultrasound signals as associated with the zone of each angularly discrete ultrasound signal, wherein each of the applied TGC curves defines a plurality of gains that maintain, increase, or decrease the angularly discrete ultrasound signal to which it the TGC curve is applied, over the timeframe of a single scan line.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

What is claimed is:

1. An ultrasound system comprising a computing device, a transducer steering mechanism and an ultrasound transducer, wherein:
    the ultrasound transducer is configured to generate angularly discrete signals over a scan region of the ultrasound system under the control of the transducer steering mechanism, for processing by the computing device;
    the computing device is communicatively coupled to the ultrasound transducer; and
    the computing device includes a processor configured to
        receive a plurality of angularly discrete ultrasound signals from the ultrasound transducer over the scan region,
        determine a scan line count corresponding to each of the received plurality of angularly discrete ultrasound signals,
        associate a Time Gain Compensation (TGC) curve from a plurality of TGC curves with each of the scan line counts, and
        apply one of the plurality of TGC curves to each of the plurality of angularly discrete ultrasound signals as associated with the scan line count of each angularly discrete ultrasound signal, wherein one TGC curve of the plurality of TGC curves is applied to one of the plurality of angularly discrete ultrasound signals associated with a first scan line count based on a user preconfiguration associating the one TGC curve to the first scan line count and a different TGC curve is applied to a different one of the plurality of angularly discrete ultrasound signals associated with a second scan line count based on the user preconfiguration associating the different TGC curve to the second scan line count, and each of the applied TGC curves defines a gain that maintains, increases, or decreases the angularly discrete ultrasound signal to which it is applied.

2. The ultrasound system of claim 1, wherein at least one TGC curve of the TGC curves is defined by a first gain value and a second gain value, the first gain value corresponds to a first distance from the ultrasound transducer, the second gain value corresponds to a second distance greater than the first distance from the ultrasound transducer, and the first gain value is less than the second gain value.

3. The ultrasound system of claim 1, wherein at least one TGC curve of the TGC curves is defined by a first gain value and a second gain value, the first gain value corresponds to a first distance from the ultrasound transducer, the second gain value corresponds to a second distance greater than the first distance from the ultrasound transducer, and the first gain value is greater than the second gain value.

4. The ultrasound system of claim 1, wherein the processor is further configured to
define a plurality of scan lines within the scan region of the ultrasound transducer, wherein each of the plurality of scan lines corresponds to one of the plurality of angularly discrete ultrasound signals and the determined scan line count, and
assign a scan line count value to each of the plurality of scan lines.

5. The ultrasound system of claim 1, wherein the processor is further configured to
define a plurality of zones having one or more scan lines within the scan region of the ultrasound transducer, and
associate each zone with one of a plurality of predefined TGC curves.

6. The ultrasound system of claim 1, wherein the processor is further configured to
generate an ultrasound image for display implementing the one or more TGC curves associated with the scan line count corresponding to each of the received plurality of angularly discrete ultrasound signals.

7. The ultrasound system of claim 1, wherein the ultrasound transducer comprises mechanical angular actuator and generates the plurality of angularly discrete ultrasound signals by a mechanical scanning mechanism.

8. The ultrasound system of claim 1, wherein the ultrasound transducer comprises a multi-element array transducer and generates the plurality of angularly discrete ultrasound signals through an electronic scanning mechanism.

9. An ultrasound system comprising a computing device, a transducer steering mechanism, and an ultrasound transducer, wherein:
the ultrasound transducer is configured to generate angularly discrete signals over a scan region of the ultrasound system under the control of the transducer steering mechanism, for processing by the computing device;
the computing device is communicatively coupled to the ultrasound transducer; and
the computing device includes a processor configured to
define a plurality of zones having one or more scan lines within the scan region of the ultrasound transducer,
receive a plurality of angularly discrete ultrasound signals from the ultrasound transducer over the scan region,
determine a zone corresponding to each of the received plurality of angularly discrete ultrasound signals,
associate a time gain compensation (TGC) curve from a plurality of TGC curves with each of the zones, and
apply one of the plurality of TGC curves to each of the plurality of angularly discrete ultrasound signals as associated with the zone of each angularly discrete ultrasound signal, wherein one TGC curve of the plurality of TGC curves is applied to a first zone based on a user preconfiguration associating the one TGC curve to the first zone and a different TGC curve is applied to a second zone based on the user preconfiguration associating the different TGC curve to the second zone, and each of the applied TGC curves define a gain that maintains, increases, or decreases the angularly discrete ultrasound signal to which it is applied.

10. The ultrasound system of claim 9, wherein at least one TGC curve of the TGC curves is defined by at least a first gain value and a second gain value, the first gain value corresponds to a first distance from the ultrasound transducer, the second gain value corresponds to a second distance greater than the first distance from the ultrasound transducer, and the first gain value is less than the second gain value.

11. The ultrasound system of claim 9, wherein at least one TGC curve of the TGC curves is defined by at least a first gain value and a second gain value, the first gain value corresponds to a first distance from the ultrasound transducer, the second gain value corresponds to a second distance greater than the first distance from the ultrasound transducer, and the first gain value is greater than the second gain value.

12. The ultrasound system of claim 9, wherein the ultrasound transducer comprises mechanical angular actuator and generates the plurality of angularly discrete ultrasound signals by a mechanical scanning mechanism.

13. The ultrasound system of claim 9, wherein the ultrasound transducer comprises an multi-element array transducer and generates the plurality of angularly discrete ultrasound signals through an electronic scanning mechanism.

14. An ultrasound system comprising a computing device and an ultrasound transducer, wherein:
the ultrasound transducer is configured to generate angularly discrete signals over a scan region of the ultrasound system, for processing by the computing device;
the computing device is communicatively coupled to the ultrasound transducer; and
the computing device includes a display, an input device, and a processor, wherein the processor is configured to
present, on the display, an ultrasound image,
receive, from the input device, designation of one or more regions within the ultrasound image,
receive, from the input device, one or more time gain compensation (TGC) curves to associate with the one or more designated regions,
receive a plurality of angularly discrete ultrasound signals from the ultrasound transducer over the scan region,
determine a zone corresponding to each of the received plurality of angularly discrete ultrasound signals,
associate a TGC curve from a plurality of TGC curves with each of the zones, and apply one of the plurality TGC curves to each of the plurality of angularly discrete ultrasound signals as associated with the zone of each angularly discrete ultrasound signal, wherein one TGC curve of the plurality of TGC curves is applied to a first zone based on a user preconfiguration associating the one TGC curve to the first zone and a different TGC curve is applied to a second zone based on the user preconfiguration associating the different TGC curve to the second zone, and each of the applied TGC curves defines a plurality of gains that maintain, increase, or decrease the angularly discrete ultrasound signal to which it the TGC curve is applied.

15. The ultrasound system of claim 14, wherein the input device is a touch sensitive component of the display thereby enabling a touchscreen interface to provide inputs to the computing device.

16. The ultrasound system of claim 14, wherein the displayed ultrasound image includes an overlay having a set of predefined regions.

17. The ultrasound system of claim 16, wherein the set of predefined regions include a plurality of zones further segmented by one or more radial distances from the ultrasound transducer.

18. The ultrasound system of claim 14, wherein at least one designated region received from the input device is a user defined region.

19. The ultrasound system of claim 14, wherein the ultrasound image is a previously captured ultrasound image.

20. The ultrasound system of claim 14, wherein the processor is further configured to generate an ultrasound image for display implementing the one or more TGC curves associated with the one or more designated regions.

21. The ultrasound system of claim 5, wherein:
the processor is further configured to
determine a zone of the plurality of zones corresponding to one or more of the determined scan line counts wherein the TGC curve applied to each of the plurality of angularly discrete ultrasound signals is further associated with the zone.

22. The ultrasound system of claim 1, wherein:
the computing device further includes a display and an input device, wherein the processor is further configured to
present, on the display, an ultrasound image,
receive, from the input device, designation of one or more regions within the ultrasound image, and
receive, from the input device, one or more time gain compensation (TGC) curves to associate with the one or more designated regions.

23. The ultrasound system of claim 22, wherein the input device is a touch sensitive component of the display thereby enabling a touchscreen interface to provide inputs to the computing device.

24. The ultrasound system of claim 22, wherein the displayed ultrasound image includes an overlay having a set of predefined regions.

25. The ultrasound system of claim 24, wherein the set of predefined regions include a plurality of zones further segmented by one or more radial distances from the ultrasound transducer.

26. The ultrasound system of claim 22, wherein at least one designated region received from the input device is a user defined region.

27. The ultrasound system of claim 22, wherein the ultrasound image is a previously captured ultrasound image.

28. The ultrasound system of claim 22, wherein the processor is further configured to generate an ultrasound image for display implementing the one or more TGC curves associated with the one or more designated regions.

\* \* \* \* \*